United States Patent [19]
Cirrillo et al.

[11] Patent Number: 6,149,054
[45] Date of Patent: *Nov. 21, 2000

[54] MECHANICAL COUNTER FOR A METERING APPARATUS

[75] Inventors: Pasquale Cirrillo; Joachim Eicher, both of Dortmund; Andreas Fiol, Wuppertal, all of Germany

[73] Assignee: Boehringer Ingelheim International GmbH, Ingelheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/091,999
[22] PCT Filed: Dec. 19, 1996
[86] PCT No.: PCT/EP96/05758
 § 371 Date: Oct. 31, 1998
 § 102(e) Date: Oct. 31, 1998
[87] PCT Pub. No.: WO97/24586
 PCT Pub. Date: Jul. 10, 1997

[30] Foreign Application Priority Data

Dec. 28, 1995 [DE] Germany .............. 195 49 033

[51] Int. Cl.⁷ ............................................ G07B 15/00
[52] U.S. Cl. .................. 235/34; 235/1 C; 128/203.15
[58] Field of Search ................... 235/1 B, 1 C, 235/34; 128/203.15, 203.12

[56] References Cited

U.S. PATENT DOCUMENTS

| | | |
|---|---|---|
| 3,078,011 | 2/1963 | Safianoff . |
| 4,817,822 | 4/1989 | Rand et al. . |
| 5,114,406 | 5/1992 | Gabriel et al. .................. 604/136 |
| 5,279,586 | 1/1994 | Balkwill .................................. 604/207 |
| 5,349,945 | 9/1994 | Wass et al. ......................... 128/200.23 |
| 5,372,128 | 12/1994 | Haber et al. ....................... 128/203.21 |
| 5,394,868 | 3/1995 | Ambrosio et al. ................. 128/203.15 |
| 5,505,195 | 4/1996 | Wolf et al. ......................... 128/203.15 |
| 5,687,710 | 11/1997 | Ambrosio et al. ................. 128/203.15 |

FOREIGN PATENT DOCUMENTS

| | | |
|---|---|---|
| 0 114 617 | 8/1984 | European Pat. Off. . |
| 1775594 | 8/1971 | Germany . |
| 40 04 904 A1 | 9/1990 | Germany . |
| 2110183 | 6/1983 | United Kingdom . |
| WO 86/05991 | 10/1986 | WIPO . |
| WO 93/21980 | 11/1993 | WIPO . |

*Primary Examiner*—Karl D. Frech
*Attorney, Agent, or Firm*—Sterne, Kessler, Goldstein & Fox P.L.L.C.

[57] ABSTRACT

A metering apparatus for metering for example a medicament requires a device with which the number of metering portions is displayed. The known display devices however are not suitable for a metering apparatus having two housing portions which are rotatable relative to each other. The mechanical counter for a metering apparatus of that kind comprises at least one spindle with rotary locking, whose axis extends in parallel relationship with the axis of the metering apparatus and which is disposed in the region of a peripheral surface of the apparatus. The spindle is automatically driven by way of a transmission assembly when the metering apparatus is actuated. The number of metering portions already discharged and the number of petering portions permitted in total is quasi-continuously displayed by the mechanical counter. The transmission ration of the transmission assembly can be designed to cover a wide range. The cursor serving for display purposes can be reset on the spindle. The permissible period of use of a metering apparatus which can be used for a plurality of supply containers can be reliably viewed.

29 Claims, 1 Drawing Sheet

MECHANICAL COUNTER FOR A METERING APPARATUS

BACKGROUND OF THE INVENTION

1. Field of the Invention

The invention concerns a mechanical counter for a metering apparatus for metering powder, liquid or gaseous substances, and metering apparatus comprising such a counter. The apparatus comprises inter alia two coaxially arranged housing portions which are rotated relative to each other upon actuation of the apparatus. The number of metering portions of the substance is counted and displayed by the counter.

An aim of the invention is to provide optimum adaptation of a counter of that kind to handling of the metering apparatus in an operationally reliable manner, and to simplify manufacture of the counter.

2. Related Art

The invention has been particularly, though not exclusively, developed for application to metered dose inhalers (MDI's) such as are disclosed in U.S. Pat. No. 5,497,944 (derived from WO91/14468), the entire contents of both of which are incorporated herein by reference. Pressure (generally at least 50 bar) is generated in a metered amount of fluid which is discharged through a nozzle assembly having one or more very small openings e.g. in the range 25 to 500 square micrometres. Preferred nozzle assemblies are disclosed in U.S. Pat. No. 5,472,143 (and parallel WO94/07607), the entire contents of both of which are incorporated herein by reference. An energy storage means, such as a spring, is preferably manually loaded e.g. by a rotary sawtooth wedge arrangement as disclosed in U.S. Pat. No. 4,260,082 and GB Patent Application 2291135, the entire contents of both of which are incorporated herein by reference. A latching mechanism is generally provided to hold the spring in the loaded position and is manually releasable to pressurise the metered amount of fluid e.g. using a piston and cylinder arrangement. A reservoir and valve arrangement can be provided for recharging the cylinder. Further details are described in PCT/EP96/04351 and parallel U.S. Ser. No. 08/726219, the entire contents of both of which are incorporated herein by reference.

Metering apparatuses are used for example in medical aerosol therapy for dealing with ailments of the respiratory tracts. In that situation a liquid or powder medicament is atomised to form an aerosol by means of an atomiser or entered into a stream of gas. The medicament is contained in a supply container which is inserted into the metering apparatus. The supply in a container may be sufficient for several days up to some months. It is therefore necessary to display the consumed amount of medicament or the amount of medicament which is still present in the container.

PCT Patent Publication WO-93/24167 provides a display device for a medical metering apparatus. That display device comprises a ring which is rotatable in coaxial relationship with respect to the apparatus and which, for each dose of a medicament under pressure which is taken from the metering apparatus, is automatically rotated through a predetermined angle by a wedge drive, a small portion of the ring being visible. The display device is pneumatically actuated when the medicament is inhaled.

U.S. Pat. No. 4,817,822 discloses a display device for a metering apparatus, the display device comprising a linear or a rotatable disk-like scale which is disposed beside the metering device and which is moved by means of a locked wheel and a locking pawl. Only a small portion of the scale is visible through a window.

PCT Patent Publication WO-86/05991 describes a display device for a metering apparatus, which device comprises a disk-like scale with teeth on the periphery of the disk, and is rotated by means of a helix member. Only a small portion of the scale is visible through a window.

PCT Patent Publication WO-92/09324 discloses a display device for a metering apparatus in which the axial movement of the supply container within the housing is transmitted by means of a locking pawl and a worm gear to a rotatable scale of which a small portion is visible through a window.

In accordance with PCT Patent Publication WO-86/02275 a display device for a medical spray apparatus comprises a digital mechanical counter which is advanced by the movement of the supply container within the housing as soon as a dose of the substance is taken from the supply container. That apparatus comprises a large number of individual parts.

A display device which is actuated pneumatically or mechanically upon displacement of the supply container, which is under pressure, in the housing of the metering apparatus, is unsuitable for a metering apparatus having two housing portions which are rotatable relative to each other and a supply container which is fixedly disposed in the metering apparatus.

Ways were therefore sought of providing a suitable mechanical counter for a metering apparatus having two housing portions which are rotatable relative to each other.

SUMMARY OF THE INVENTION

The invention provides according to one aspect, a mechanical counter for a metering apparatus having two coaxially arranged housing portions which are rotatable relative to each other, which includes at least one spindle, whose axis extends substantially parallel to the axis of the metering apparatus, and which is disposed in the region of the peripheral surface of the metering apparatus and which is mounted to the first housing portion in the vicinity of each of the spindle ends by means of a respective rotary mounting. The spindle has a tooth arrangement at the end which is closest to the second housing portion. Provided at the edge of the second housing portion is at least one projection which engages into the tooth arrangement at the spindle end upon rotation of the two housing portions relative to each other. In order to provide good running properties for the transmission assembly, the tooth arrangement at the spindle end and the projections are preferably in the form of an involute tooth configuration. Disposed on the spindle is a cursor with rotary securing (prevention of rotation), a scale being disposed opposite same.

According to another aspect, the invention provides a metering apparatus having two coaxially arranged housing portions which are rotated relative to each other when the metering apparatus is operated, the metering apparatus having a mechanical counter comprising a screwthreaded spindle mounted in bearing means on one of the housing portions in a peripheral region thereof so that it is rotated by movement of the other housing portion, and a cursor movable, by the screwthread, relative to marker means, the arrangement being such that movement of the cursor with respect to the marker means provides a measure of the number of operations of the apparatus.

Preferred features of the counter and the metering apparatus will now be described.

The two housing portions are rotated relative to each other to actuate the metering apparatus. The angle of rotary movement may be a preferably integral fraction of 360 degrees; it is preferably 30 to 360 degrees. The relative movement of the two housing portions relative to each other, is taken off and converted into a rotary movement of the spindle and a sliding movement of the cursor by means of the transmission assembly which comprises the tooth arrangement at the one end of the spindle and the at least one projection at the edge of the second housing portion. The rotary mountings for the spindle are preferably in the form of snap-action mountings. The transmission ratio of the projection-type transmission assembly is fixed by the number of projections and the number of teeth on the pinion; that also fixes the number of revolutions of the spindle, which corresponds to an actuation of the metering apparatus. For each actuation of the metering apparatus the number of revolutions of the spindle can be from 1/30th (one thirtieth) to 10. The pitch of the screwthread on the spindle is adapted to the number of metering portions which can be taken from the supply container in the metering apparatus, and to the travel of the cursor on the spindle. When the spindle is rotated the cursor on the spindle is displaced relative to the scale which is disposed for example on the first housing portion. The scale is preferably linearly divided. The position of the cursor indicates what proportion of the substance to be metered has already been taken from the supply container and what proportion is still present. The direction of rotation of the screwthread on the spindle is either in the same direction or in the opposite direction to the direction of rotation of the housing portions relative to each other.

The cursor substantially comprises a display ring, at least one limb having a screwthread portion and at least one further limb with a resetting projection. There are preferably a plurality of limbs and the limbs are preferably of a resilient nature. The screwthread portion positively lockingly engages into the screwthread on the spindle. The cursor can be displaced on the spindle for resetting thereof, by means of the resetting projection. When the cursor is displaced the screwthread portions on the resilient limbs slide resiliently over the spindle screwthread without damage. The contours of the cursor and the housing are so selected that the cursor is prevented from being rotated on the spindle, by positively locking engagement. For example at least one of the resetting projections may project beyond the screwthread to such a degree that it does not pass through the gap between the spindle and the peripheral surface of the first housing portion. That projection serves as a rotary securing means for the cursor.

A recess can be provided at the other end of the spindle which is in opposite relationship to the drive portion of the spindle. As soon as the screwthread portions on the resilient limbs have reached that recess the cursor ceases to be displaced. The recess serves as a free-motion means for the cursor so that damage to the cursor is avoided if the admissible travel distance of the cursor on the spindle is exceeded upon further actuation of the metering apparatus.

Preferably a cover can be fitted over the first housing portion to protect the metering apparatus and the counter. The cover is connected to the first housing portion releasably in an axial direction in a predetermined position. The cover when in the condition of being fitted in position cannot rotate relative to the first housing portion. Accordingly the first housing portion can still be rotated with respect to the second housing portion although the first housing portion is covered by the cover.

The scale which is disposed opposite the cursor is provided either on the first housing portion or on the inside or the outside of the cover. The cover is transparent in a region-wise manner or it comprises transparent material.

At least one rigid entrainment means may be provided on the inside of the cover, which entrainment means pushes the cursor back into the starting position thereof at the one end of the spindle by means of the resetting projections when the cover is fitted into place.

Elastic entrainment means may be provided in place of the rigid entrainment means. In this case the resetting projections of the cursor can be provided with rigid limbs.

When the cursor is reset the cursor abuts against a step at the one end of the spindle before the cover reaches its end position. The cover is further moved to its end position, in which case the elastic portion, that is to say the resilient limb or the elastic entrainment means, springs back and the cursor and the entrainment means are uncoupled. Accordingly the cursor is in its starting position from which it is displaced when the spindle is rotated.

In a specific configuration of the counter the pinion at the one end of the spindle has four teeth of which two oppositely disposed teeth are wider than the other two teeth. Provided on the edge of the second housing portion are two projections, between which there is a recess in which the wider teeth of the pinion can roll. That transmission assembly preferably has a transmission ratio of half a spindle revolution to two actuations of the metering apparatus, for example half a revolution to a rotary movement of 360 degrees of the two housing portions relative to each other.

If a rotational movement of for example 120 degrees of the two housing portions relative to each other is required for actuation of the metering apparatus there may be three projections on the second housing portion, more specifically being displaced through 120 degrees relative to each other. Furthermore in this case also the projections on the second housing portion may be present only singly. Then the spindle is further rotated only in each third actuation of the metering apparatus, although each actuation is counted.

The flanks of the wider teeth lie on the inner or outer peripheral surface of the second housing portion. The spindle is therefore rotatable only when the wider teeth can engage into the opening between the projections. That rotary locking arrangement always holds the spindle in the starting position which is provided at the beginning of the rotary movement.

A plurality of supply containers containing the substance to be metered can possibly be successively fitted into the metering apparatus and used. If the substance to be metered is for example a medicament it may be necessary for reasons of hygiene to limit the permitted number of metering portions with the re-usable metering apparatus. Then it is additionally necessary to count and display the total number of metering portions which have already been discharged with the metering apparatus or the total number of metering portions which are still available. The above-described mechanical counter can be developed in various ways to cover that situation.

In a first embodiment of such a development a gear is provided on the other end of the spindle, which is opposite to the drive side. Provided at the corresponding end of the first housing portion is a coaxial ring gear, preferably with a flange, which is mounted rotatably with respect to the first housing portion and into which the gear engages. The ring gear is also rotated through a given angle for each revolution of the spindle.

Provided on the flange is at least one first mark which, after less than a 360 degree rotation of the ring gear relative to the first housing portion and after consumption of a supply container is disposed opposite a second mark which is in a fixed position relative to the first housing portion. The number of marks on the flange is equal to the number of supply containers which are permitted as a maximum for the metering apparatus (or for the substance to be metered). The second mark can be disposed on the first housing portion or it can be a window in the cover which is fitted onto the first housing portion.

The flange can be provided, instead of the marks, with a scale which quasi-continuously displays the total number of metering portions discharged with the metering apparatus or the total number of metering portions still available, for example in a window. The ring gear is rotated through at most 360 degrees to display the maximum permissible metering portions. For that purpose, a high step-up ratio is possibly required between the rotation of the spindle and the rotation of the ring gear, that ratio being structurally fixed by means of a suitable ratio between the numbers of teeth involved.

In a second embodiment of the development of the counter the counter includes a second spindle which may be similar to and arranged parallel to the first spindle and which carries a cursor which is possibly not resettable. Provided at one of the two ends of the first spindle is a gear which engages into a gear at the corresponding end of the second spindle. Disposed opposite the cursor on the spindle is a scale in a fixed position with respect to the first housing portion, which scale can be disposed either on the first housing portion or on the cover fitted thereon. In the case of this counter the total number of metering portions which have already been discharged or the total number of metering portions which are still available is represented on the displacement travel of the cursor on the second spindle.

In place of the second spindle with cursor, the arrangement may have a rotatably mounted roller, on the periphery of which a helical line is drawn with an entire revolution over the entire length of the roller. The surfaces on the two sides of the helical line are marked in different ways, preferably in two colours, for example red and white or red and green. In this construction the cover has a narrow window which is as long as the roller and through which a narrow strip of the peripheral surface of the roller is visible. A scale can be disposed beside the window and extends over the entire length of the roller. The scale can be divided in accordance with the maximum permitted number of metering portions or it can be divided into numbered sections according to the maximum permitted number of supply containers.

A third embodiment of the development of the counter has a second spindle which is of a similar design configuration to the first spindle but which is disposed at another location in the region of the peripheral surface of the metering apparatus. It is provided with a transmission arrangement, similarly to the first spindle, but the transmission ratio is matched to the total number of permissible metering portions. That spindle is driven by projections at the edge of the second housing portion, preferably by the projections which are already used for driving the first spindle.

In order to provide the high step-up ratio which is possibly required between the first and second spindles or between the first spindle and the ring gear, the arrangement may have, instead of the gear on the first spindle, a single-tooth transmission arrangement with which the gear on the second spindle or the ring gear is further rotated by one tooth for each revolution of the first spindle. The step-up ratio can be from 2 to 1 to 10 to 1.

The rotary locking means for the spindle or the ring gear (i.e. the means for inhibiting unwanted movement) may be a locking pawl or the rotary locking means lies in the friction between the spindle and the mounting or the ring gear and the mounting or in a specific configuration of the parts, for example a positively locking tooth configuration. The cursor is rotationally secured on the spindle by virtue of the positively locking contour of the cursor.

The components of the counter may consist of virtually any material. They are preferably made from plastics material, for example by an injection moulding process. For medical purposes, physiologically harmless materials are used such as for example polybutyleneterephthalate (PBT) or a compound of PBT and Teflon (polytetrafluoroethylene). The materials are preferably so selected that different materials run against each other, for example PBT with Teflon against PBT or PBT against acrylbutadiene-styrene.

The counter according to the invention can be used for example in a metering apparatus which serves as a high-pressure atomiser for a liquid medicament. The liquid to be atomised is disposed in a pressure-less supply container which communicates with a miniaturised high-pressure generating means with which an aerosol is generated; for details in this respect see German laid-open application (DE-OS) No. 195 36 902.5 (the entire contents of which are incorporated herein by reference). The device for producing the high pressure is operated by means of a spring-actuated locking stressing mechanism, the spring being stressed by rotation of two housing portions relative to each other; for details attention is directed to German laid-open application (DE-OS) No. 195 45 226.7 (the entire contents of which are incorporated herein by reference). The counter according to the invention is automatically advanced when the housing portions are rotated relative to each other.

DETAILED DESCRIPTION OF THE DRAWING

Figure 1:
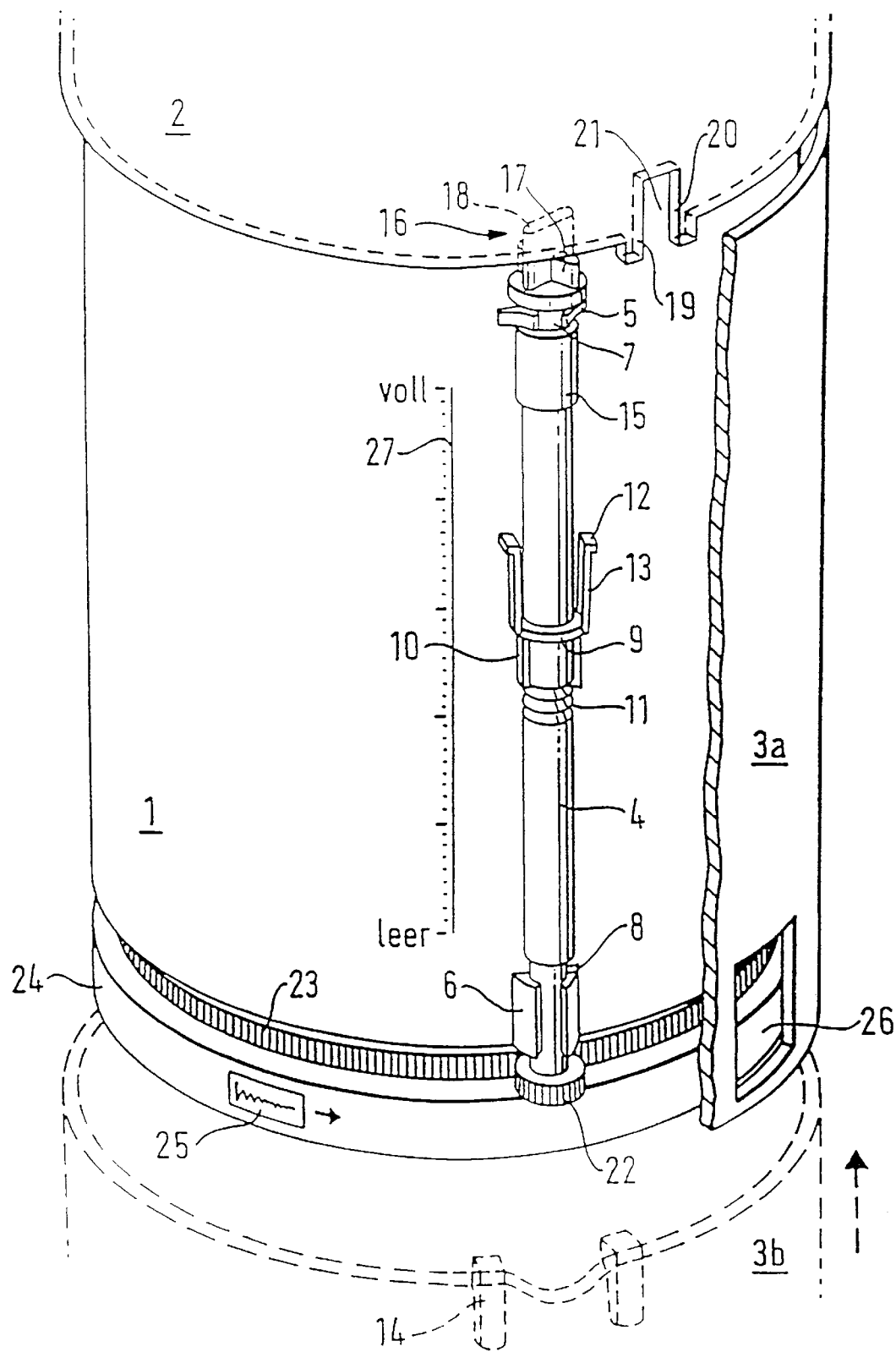
FIG. 1 Perspective view of a part of a metering apparatus having a counter

A preferred embodiment of the invention will now be described in greater detail with reference to the drawing (FIG. 1) which shows part of a metering apparatus having a counter. In this embodiment the first housing portion is rotated through 180 degrees relative to the second housing portion for actuation of the metering apparatus.

The first housing portion 1 is mounted coaxially rotatably relative to the second housing portion 2. The cover 3a which is mounted thereon encloses the first housing portion 1 and the counter. The cover is additionally shown in broken lines in the withdrawn position 3b. The number of metered portions taken from the supply container which is in use at the time is counted with the spindle (rotary shaft) 4. The spindle 4 is rotatably mounted on the first housing portion by the two snap-action mountings 5 and 6 which act as bearings. The groove 7 which accommodates mounting 5 serves for axially fixing the spindle. The cursor with display ring 9 is provided with two resilient limbs 10 each having a respective screwthread engagement portion 11 and two resetting projections 12 on two limbs 13. The recess 8 is the free-motion means for the portions 11 at the end of their travel. Provided on the inside of the cover are two entrainment means 14 which, when the cover is fitted in position, push the cursor 9 back into the starting position at the end of the spindle by means of the resetting projections 12. When that happens the cursor ring 9 bears against the abutment 15 and the cursor is released as described above.

Disposed at the one end of the spindle is a four-tooth pinion 16 having two (axially) narrow teeth 17 and two (axially) wide teeth 18. The edge of the second housing portion carries the two projections 19 and 20 between which there is the opening 21. As described aboave, the teeth and projections are preferably of involute shape. Disposed at the other end of the spindle is the gear 22 which engages into the ring gear 23. Provided on the flange 24 of the ring gear are a plurality of numbered marks 25, of which a respective mark appears in the window 26 in the cover 3a after a given rotary movement of the ring gear.

The position of the cursor 9 against marker means in the form of the labelled scale 27 shows the number of metering portions taken from the supply container or the number of metering portions which can still be taken therefrom. When the supply container is empty a respective one of the numbered marks 25 appears in the window 26.

The illustrated counter incorporates the preferred features of the invention discussed above (but not the second and third "developments" discussed above) and the description just given should be read in conjunction with earlier discussion of these preferred features.

The preferred counter according to the invention has the following advantages:

- it is automatically advanced when the metering apparatus is actuated;
- it is non-critical in terms of tolerances and is therefore reliable and sure in operation;
- the transmission can be designed to cover a wide range;
- it displays the number of discharged metering portions and/or the number of metering portions still available, quasi-continuously and with an adequate degree of accuracy;
- it is inaccessible and cannot be displaced by mistake when using the metering apparatus;
- it can be used for a plurality of supply containers in succession;
- it can be produced for a different number of metering portions from each supply container and for a different maximum number of supply containers which may be used with a metering apparatus;
- it is integrated into the metering apparatus and does not require any substantial modification thereof;
- it can be produced in miniaturised form and therefore takes up only a small amount of space;
- the individual parts of the counter,are preferably made from plastics material which operate without lubricant at a low level of friction;
- no substances can get into the substance to be metered, from the counter;
- it comprises a small number of individual parts which can be inexpensively produced by injection moulding;
- it is easy to assemble;
- the counter can be reset each time a supply container is emptied; as a result the starting position of the cursor on the spindle is clearly established whenever a fresh supply container is introduced;
- the combination of a spindle which counts the actuations of the metering apparatus during use of a supply container with a second spindle or with a ring gear means that the metering apparatus can be reliably used for a predetermined total number of metering portions or for a predetermined total number of supply containers in succession. The period of use of the metering apparatus can be reliably reviewed.

What is claimed is:

1. A mechanical counter for a metering apparatus having a first housing portion and a second housing portion coaxially arranged which are rotated relative to each other when the metering apparatus is operated, the mechanical counter comprising:

a spindle with a screwthread thereon, an axis of which extends substantially parallel to an axis of the metering apparatus and which is disposed in the region of a peripheral surface of the metering apparatus and which is mounted in the vicinity of ends of the spindle with respective rotary mountings on the first housing portion;

at least one projection at an edge of the second housing portion, for engaging a tooth arrangement and rotating the spindle;

a cursor movable along the spindle by the screwthread when the spindle rotates; and a scale disposed adjacent to the cursor.

2. A mechanical counter according to claim 1 wherein said rotary mountings are snap-action mountings.

3. A mechanical counter according to claim 1, wherein one end of the spindle in the vicinity of the second housing portion is provided with a pinion, said pinion being provided with said tooth arrangement; and wherein said at least one projection engages with said tooth arrangement as the two portions are rotated relative to each other.

4. A mechanical counter according to claim 3, wherein said tooth arrangement on said pinion includes four teeth, and said at least one projection on the second housing portion comprises two projections.

5. A mechanical counter according to claim 3, wherein said pinion includes four teeth of which two oppositely disposed teeth are wider than the other two teeth, and wherein a flank of the wider teeth bears against an inner peripheral surface of the second housing portion, said at least one projection comprises two projections on the edge of the second housing portion, and wherein an opening between the two projections is larger than the width of the wider teeth of the pinion.

6. A mechanical counter according to claim 1, further comprising a transmission ratio of half a spindle revolution to two actuations of the metering apparatus.

7. A mechanical counter according to claim 1 wherein a pitch on the spindle screwthread is matched to the number of the metering portions and a displacement travel of the cursor.

8. A mechanical counter according to claim 1 wherein the spindle includes means for inhibiting unwanted movement.

9. A mechanical counter according to claim 1 wherein the cursor comprises a screwthread engagement portion engageable with the screwthread on the spindle, and a resilient limb.

10. A mechanical counter according to claim 9 wherein the end of the spindle furthest from said second housing portion comprises a recess for receiving the screwthread engagement portion of the cursor.

11. A mechanical counter according to claim 9 comprising a resetting projection on the the resilient limb.

12. A mechanical counter according to claim 1 further comprising a cover for the first housing portion, wherein said cover is receivable over the first housing portion in the axial direction to cover over the spindle, and wherein said cover is transparent in a region-wise manner or comprises transparent material.

13. A mechanical counter according to claim 12 further comprising entrainment means on the inside of the cover.

14. A mechanical counter according to claim 1 further comprising a second spindle with means for inhibiting unwanted movement, said second spindle being arranged in substantially parallel relationship with the first spindle, a cursor secured against rotation on the second spindle, a one-tooth transmission assembly including a projection wheel at one end of the first spindle, and a gear at the corresponding end of the second spindle with which the projection wheel at the end of the first spindle engages, and a scale which is disposed adjacent the cursor on the second spindle.

15. A mechanical counter according to claim 14 wherein the second spindle comprises a roller on which a helical line is drawn with one revolution over the entire length of the roller and the surfaces on the two sides of the helical line are marked in different ways, and the counter comprises a narrow transparent strip in a cover axially receivable over the first housing portion through which a strip on the peripheral surface of the roller is visible.

16. A mechanical counter according to claim 1 further comprising a gear on the end of the spindle furthest from the second housing portion, and a ring gear with which the gear engages, said ring gear comprising means for inhibiting unwanted movement, and preferably a flange;

wherein said ring gear is mounted coaxially with the first housing portion and is rotatable with respect thereto.

17. A mechanical counter according to claim 16 further comprising a first marking on the flange of the ring gear, which marking, after less than 360 degree rotation of the ring gear relative to the first housing portion, is disposed opposite a second marking which is in a fixed position relative to the first housing portion.

18. A mechanical counter according to claim 17 wherein said second marking is on the first housing portion.

19. A mechanical counter according to claim 17 wherein said second marking comprises a window in a cover axially receivable over the first housing portion.

20. A mechanical counter according to claim 1 further comprising a second spindle with means for inhibiting unwanted movement, said second spindle being arranged in a substantially parallel relationship with the first spindle, a cursor secured against rotation on the second spindle, and a one-tooth transmission assembly including a tooth arrangement at an end of the second spindle which is closest to the second housing portion, and projections at the edge of the second housing portion which engage with the tooth arrangement at the end of the second spindle upon rotation of the housing portions relative to each other.

21. A metering apparatus having two coaxially arranged housing portions which are rotated relative to each other when the metering apparatus is operated, the metering apparatus having a mechanical counter comprising:

a spindle with a screwthread thereon, an axis of which extends substantially parallel to an axis of the metering apparatus and which is disposed in the region of a peripheral surface of the metering apparatus and which is mounted in the vicinity of ends of the spindle with respective rotary mountings on a first of said two housing portions;

at least one projection at the edge of a second of said two housing portions, for engaging a tooth arrangement and rotating the spindle;

a cursor movable along the spindle by the screwthread when the spindle rotates; and a scale disposed adjacent to the cursor.

22. A metering apparatus according to claim 21 which is a metered dose inhaler.

23. A metering apparatus having two coaxially arranged housing portions which are rotated relative to each other when the metering apparatus is operated, the metering apparatus having a mechanical counter comprising a screwthread spindle mounted in bearing means on one of the housing portions in a peripheral region thereof so that it is rotated by movement of the other housing portion, and a cursor movable, by the screwthread, relative to marker means, the arrangement being such that movement of the cursor with respect to the marker means provides a measure of the number of operations of the apparatus.

24. A metering apparatus according to claim 23, wherein the cursor can be temporarily released from the screwthread for resetting.

25. A metering apparatus according to claim 23, including means for indicating the number of times the cursor has moved through its path of travel.

26. A metering apparatus according to claim 23 wherein the spindle axis is substantially parallel to the axis of rotation of the housing portions and the spindle has a gear thereon which cooperates with means on said other housing portion to effect rotation of the spindle.

27. A metering apparatus according to claim 26 wherein the spindle is rotated during only part of the relative rotation of the housing portions.

28. A metering apparatus according to claim 23 which is a metered dose inhaler.

29. A mechanical counter according to claim 1, wherein the cursor is resettable.

* * * * *

UNITED STATES PATENT AND TRADEMARK OFFICE
CERTIFICATE OF CORRECTION

PATENT NO. : 6,149,054　　　　　　　　　　　　　　　　　　　　　　Page 1 of 1
DATED : November 21, 2000
INVENTOR(S) : Cirillo et al.

It is certified that error appears in the above-identified patent and that said Letters Patent is hereby corrected as shown below:

Title page,
Under item [75] inventors, delete "Cirrillo" and insert -- Cirillo --.

Column 3,
Line 4, after "other" delete ",".

Signed and Sealed this

Thirtieth Day of October, 2001

Attest:

NICHOLAS P. GODICI
Acting Director of the United States Patent and Trademark Office Attesting Officer